United States Patent [19]

Morales et al.

[11] Patent Number: 5,120,316
[45] Date of Patent: Jun. 9, 1992

[54] URETHRAL CATHETER AND CATHETERIZATION PROCESS

[75] Inventors: Alvaro Morales, Kingston, Canada; Michael G. Hanna, Jr., Frederick, Md.

[73] Assignee: Akzo N.V., Arnhem, Netherlands

[21] Appl. No.: 589,721

[22] Filed: Sep. 28, 1990

[51] Int. Cl.⁵ .................................... A61M 37/00
[52] U.S. Cl. ............................ 604/148; 604/256; 604/244
[58] Field of Search .................... 604/51, 54, 55, 148, 604/87, 88, 96, 101, 102, 187, 244, 246, 247, 256, 264, 266, 268, 278, 93

[56] References Cited

U.S. PATENT DOCUMENTS

| | | | |
|---|---|---|---|
| 1,642,950 | 9/1927 | Haas | 604/244 X |
| 3,438,375 | 4/1969 | Ericson | 604/268 X |
| 4,248,234 | 2/1981 | Assenzu et al. | 604/256 X |
| 4,301,797 | 11/1981 | Pollack | 604/256 X |
| 4,630,609 | 12/1986 | Chin | 604/101 X |
| 4,723,946 | 2/1988 | Kay | 604/247 X |
| 4,737,152 | 4/1988 | Alchas | 604/256 |
| 4,759,752 | 7/1988 | Stöber | 604/247 |
| 4,850,982 | 7/1989 | Erlich et al. | 604/256 |

Primary Examiner—John D. Yasko
Assistant Examiner—Adam J. Cermak
Attorney, Agent, or Firm—Spencer & Frank

[57] ABSTRACT

A device for delivering medication into a human body, comprising a catheter having proximate and distal ends, and first and second lumina extending substantially the entire length of the catheter. A first opening in the catheter near its distal end drains fluid from a body when the catheter is inserted therein. There is a second opening in the catheter between the first opening and the distal end of the catheter. The second opening is fluidly connected with the second lumen. A diaphragm is located adjacent to the second opening for blocking off the second opening from the second lumen, and the diaphragm is burstable by a predetermined pressure for unblocking the second opening for fluidly connecting it with the second lumen. Thus, medications can be safely administered without the possibility of premature contact of the medication with the body. The catheter is particularly well suited to the administration of toxic substances such as BCG vaccine into the bladder of bladder cancer patients.

16 Claims, 3 Drawing Sheets

URETHRAL CATHETER AND CATHETERIZATION PROCESS

BACKGROUND OF THE INVENTION

This invention relates to a urethral catheter, and to a method of delivering medication such as infectious vaccines, bacillus Calmette-Guerin (BCG) for example, vaccine, into the bladder for treating bladder cancer.

Urethral catheters are known for insertion through the urethra into the bladder for administering medication or radiopaque dyes into the bladder. Drawbacks of known urethral catheters include catheter traumatization of the urethral canal by the insertion and presence of the catheter in the urethra. In addition, inflammation and infection of the urethra can result from fluids passing from the catheter and into contact with the irritated urethra.

Previous attempts to prevent urethral infection include the indwelling urinary catheter disclosed in U.S. Pat. No. 4,579,554, in which deep grooves are provided along the length of the catheter for washing and cleansing the outside of the catheter so that the mucosa of the penile urethral canal is irrigated to reduce infection. Furthermore, a balloon is attached to the distal end of the catheter for being inflated when the catheter is in place in the bladder. The balloon both anchors the catheter and seats snugly against the wall of the bladder to resist escape of infected fluids into the sterilely treated urethra. This catheter is apparently designed chiefly for draining the bladder over a period of time, and has no mechanism for ensuring that a medication is not prematurely administered.

A catheter such as in the above-described U.S. Pat. No. 4,579,554 could not be safely used for administering BCG into the bladder of bladder cancer patients. BCG is highly toxic, and has been known to result in death when prematurely released within the urethra in the event of catheter traumatization. Given that the indwelling urinary catheter has a permanently open flow aperture at the distal end, leakage of BCG could occur through that opening while the catheter is being inserted through the urethra before the distal end is completely within the bladder, resulting in infection and, perhaps, death.

SUMMARY OF THE INVENTION

It is an object of the invention to provide an improved catheter for the administration of medications only at the intended location.

This object is achieved by the provision of a novel design in which the distal end of the catheter contains an opening sealed with a rupturable diaphragm through which the concentrated medication is administered. Inboard from the sealed opening is an opening through which fluids can be drained from the bladder. Each opening is connected to the opposite end of the catheter through a separate channel through which fluids can pass. The present invention ensures that the diaphragm is not ruptured, such as by bursting under pressure, until the distal end of the catheter is properly positioned. Proper positioning is indicated by urine draining through the catheter, which can only happen after the opening for drainage has entered the bladder. After proper placement is indicated by urine drainage, the drainage channel can be sealed and pressure applied to burst the diaphragm, after which the concentrated medication can be administered. The structure of the catheter ensures that no concentrated potentially toxic medication, such as BCG, is prematurely introduced; first, because the drainage opening is placed inboard no urine can drain from the bladder unless the catheter with the sealed opening is inside the bladder, and second if the diaphragm sealing the first opening is against the inside wall of the urethra the diaphragm can not be distended enough to rupture.

The novel diaphragm covering the opening at the distal end of the catheter can be disposed within the catheter for blocking the medication dispensing passage, or can be disposed substantially on the outer surface of the catheter for blocking the opening in the wall of the catheter through which the medication is dispensed. The only limitation is that it must be distended outwardly from the surface of the catheter on application of pressure from within the catheter before the diaphragm can rupture.

The invention further includes a novel process for treating bladder cancer that prevents highly toxic, concentrated BCG from entering the urethra from the catheter used in the treatment. The novel method includes delivering concentrated bacillus Calmette-Guerin (BCG) vaccine into the bladder of patients by first inserting a urethral catheter, having at least two lumina extending substantially the entire length thereof, through the urethra into the bladder. Next, after urine drainage has been noted through a first one of the at least two lumina, the first lumen is sealed to prevent drainage after BCG is introduced, and pressure is applied through the second one of the two lumina to burst a diaphragm sealing off the second lumen, after which BCG is administered into the bladder. The opening through which BCG is administered is assured of having been placed within the bladder, as the opening through which urine is drained is located inboard from the opening sealed by the diaphragm.

In practice, the entire catheter is then withdrawn completely, and after about two hours the patient is allowed to urinate normally, as that time period is generally sufficient for the administered BCG to have caused the inflammation response which results in the sloughing off or the destruction of the tumor.

DESCRIPTION OF THE PREFERRED EMBODIMENTS

Figure 1:
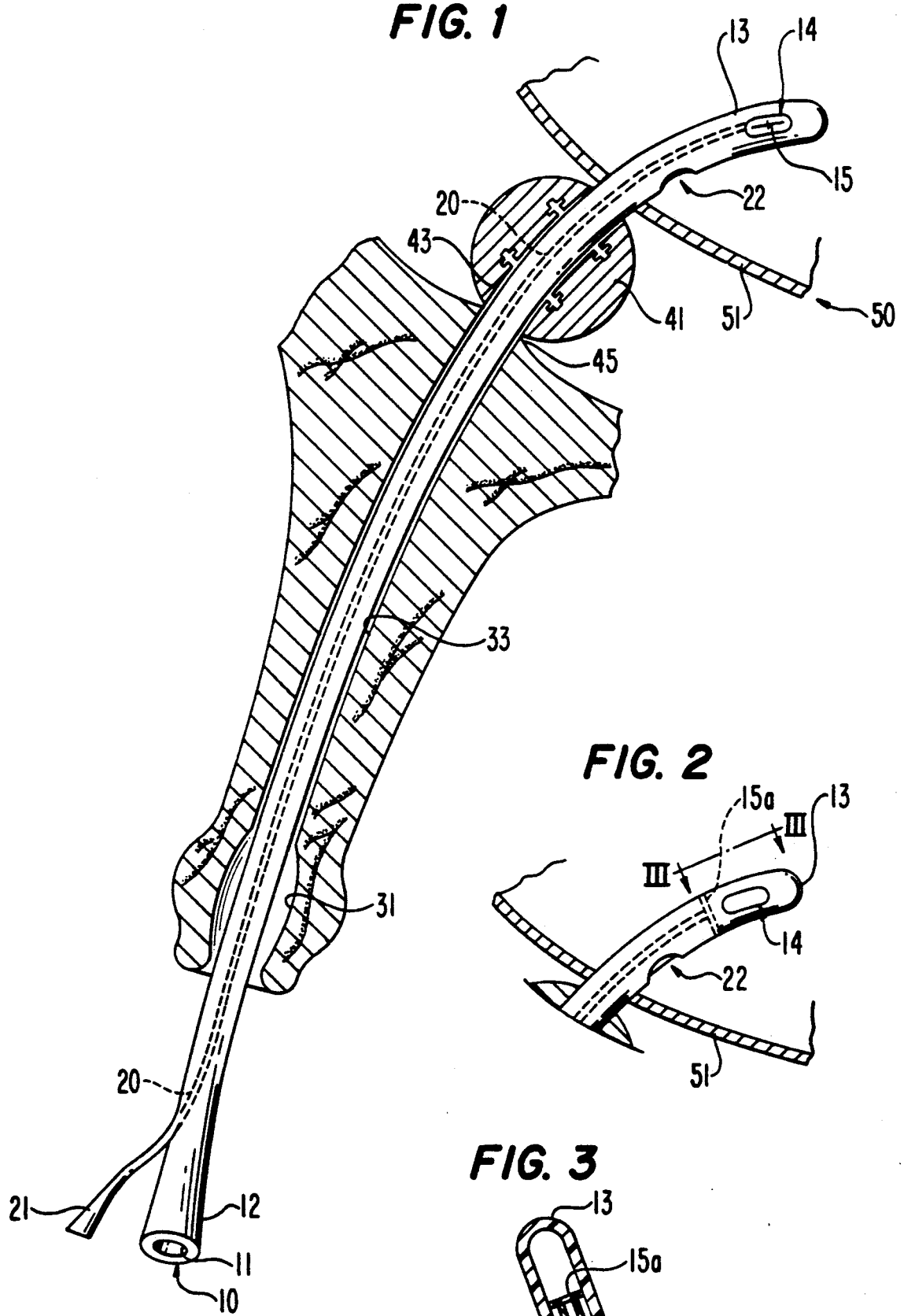
FIG. 1 illustrates an embodiment of the urethral catheter of the present invention.

Turning to FIG. 1, urethral catheter 10 of the present invention is shown already inserted in the bladder of a male bladder cancer patient. Urethral catheter 10 has an opening 22 disposed at distal end 13. A first lumen 11 of a plurality of lumina extends substantially the entire length of catheter 10, and first lumen 11 serves as a urine drainage conduit, inasmuch as first lumen 11 is fluidly connected to opening 22. Fitting 21 is adapted to be attached to a pressure apparatus for pressurizing and bursting the diaphragm. Fitting 21 can be clamped off, as required.

A second lumen 20 of the plurality of lumina extends along the entire length of catheter 10 and serves as a conduit through which medication M, for example, BCG is administered after the noting of urine drainage out of proximal end 12 of lumen 11. The proximal end of catheter 10 is adapted to be clamped off, or otherwise sealed against fluid loss, after injection of BCG into the bladder. At distal end 13 an opening 14 is provided that is fluidly connected with medication conduit 20 and is covered by rupturable diaphragm 15. Diaphragm 15 is burstable at a pressure greater than the pressure that would be required to inflate diaphragm 15 within the urethra. Thus, diaphragm 15 can not be inadvertently burst within the urethra because it cannot first be distended. To ensure that diaphragm 15 bursts and opens in a controlled manner, two grooves or crossed score lines can be cut or embossed in the surface of diaphragm 15. The weakening of diaphragm 15 by scoring reduces the possibility that pieces of the diaphragm may break off, as in an uncontrolled break, and be expelled into the bladder. Thus, the introduction of undesirable, foreign matter into the bladder is avoided.

Figure 2:
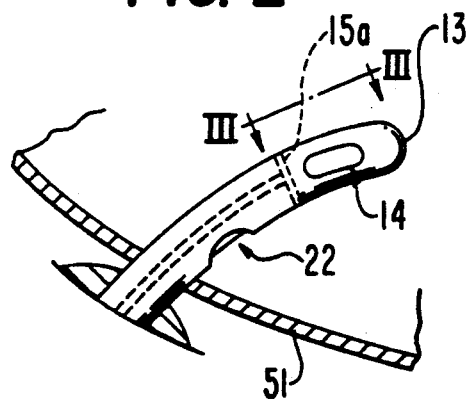
FIG. 2 illustrates a further embodiment of the invention.
Figure 3:
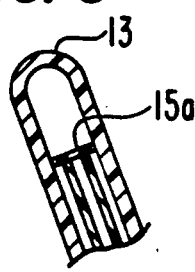
FIG. 3 illustrates a partial sectional view taken along line III—III of the embodiment of FIG. 2.

Turning to FIG. 2, a further embodiment of the invention is shown in which diaphragm 15a is a wall disposed within catheter 10 at the distal end 13 thereof completely blocking medication conduit 20 prior to rupturing diaphragm 15a in a manner similar to the rupturing of diaphragm 15 in the embodiment of FIG. 1. A cross section of a portion of distal end 13 is shown in FIG. 3.

Figure 7:
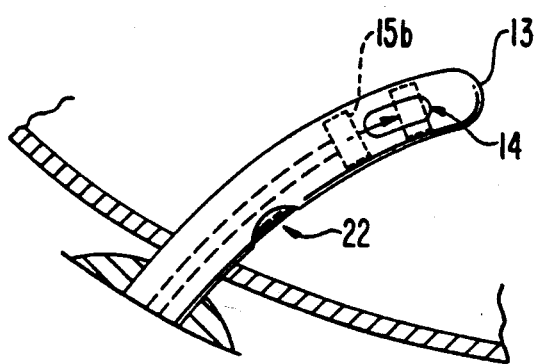
FIG. 7 illustrates another embodiment of the invention.

A still further embodiment of the invention as shown in FIG. 7, substitutes a slidable plug 15b in place of diaphragm 15a. Such a slidable plug would be positioned in a location such as shown in FIGS. 2 and 3, and would normally block conduit 20, except when a sufficiently high pressure is applied for sliding the plug further toward the distal end of catheter 10 to fluidly connect opening 14 with the proximal end of conduit 20.

In use, for example, in a male bladder cancer patient as shown in FIG. 1, urethral catheter 10 is inserted into the patient in a manner similar to the known fashion. Distal end 13 is initially inserted into the lacuna navicularis 31, and along the entire length of the penile urethral canal 33, through the membranous urethra 45, the prostatic urethra 43 of prostate gland 41, the outer bladder wall 51, and finally into bladder 50.

Figure 4A:
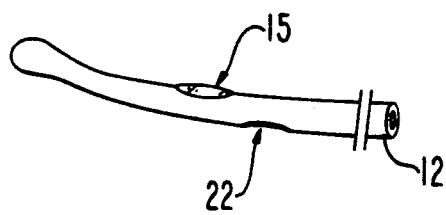
FIGS. 4A—4D schematically illustrate the administration of medication with the embodiment of FIG. 1.

After opening 22, and, hence, distal end 13 and opening 14, are disposed within the bladder 50, as schematically shown in FIG. 4A, fluid, i.e., urine, drains through conduit 11. If, somehow, diaphragm 15 is inadvertently not in the bladder 50 when the attempt is made to inflate and to rupture it, as when distal end 13 is still within urethral canal 33, the diaphragm can not be inflated prematurely, and burst, thanks to the strength of the walls of the urethra relative to the predetermined bursting strength of diaphragm 15. Accordingly, under those conditions, there will be positive feedback that the distal end 13 is not properly positioned within the bladder 50, and the catheter 10 will be inserted further into the patient's urethra. Thus, the risk of toxic BCG being inadvertently administered in the urethral canal 33 is eliminated.

Figure 4B:
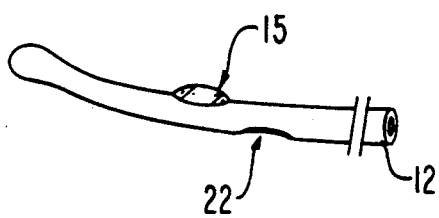
Figure 4C:
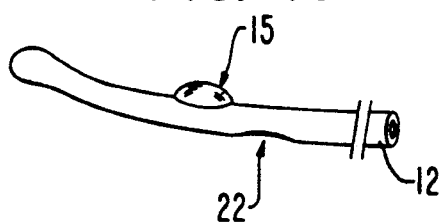
Figure 4D:
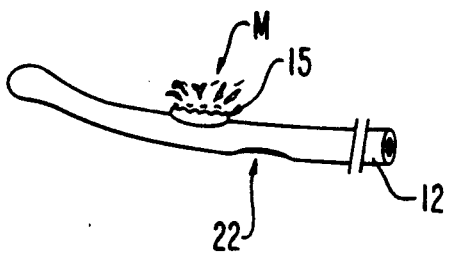
Figure 5:
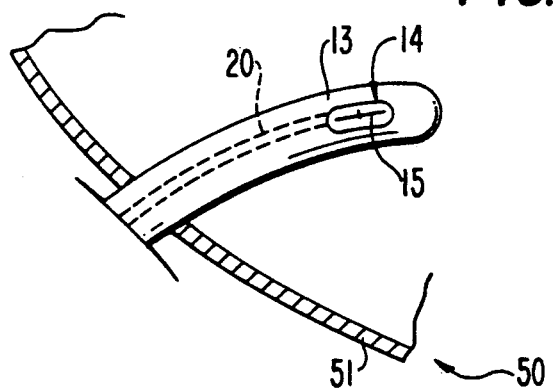
FIG. 5 illustrates a further embodiment of the invention.

When opening 22 is completely within the bladder 50, urine will normally drain through conduit 11. At that time, as opening 14 is closer to the distal end 13 of catheter 10, the presence of urine indicates opening 14 is completely within the bladder. Then, pressure is applied at proximal end 12 of catheter 10 through medication conduit 20 and diaphragm 15 begins to distend, as shown in FIG. 4B. The greatest distension of diaphragm 15, under maintained pressure, is illustrated in FIG. 4C. As shown in FIG. 4D, the applied pressure, which should be lower than the pressure that would be required to distend diaphragm 15 if it is against the wall of the urethra, ruptures diaphragm 15 along the weakened score lines, and BCG, or other medication M, is then safely administered. It is an additional structural safety feature that the pressure required for distending and bursting diaphragm 15 is sufficiently low to ensure that diaphragm 15 is not prematurely burst while still within the urethra. Thus, the inboard or "less distal" location of the hole 22 for draining urine, along with the selection of a suitable distending and bursting strength for diaphragm 15, provide dual safety features.

In an alternative embodiment the proper selection of materials and material thickness for diaphragm 15 can eliminate the need for score lines.

Figure 6:
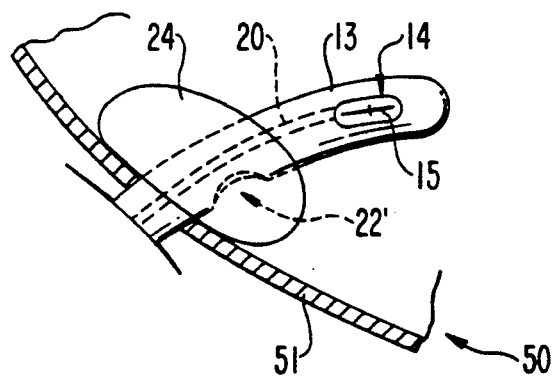
FIG. 6 illustrates a still further embodiment of the invention.

In another alternative preferred embodiment, illustrated in FIG. 6, only one lumen 20 is used. The embodiment of FIG. 6 differs from the embodiment of FIG. 1 only in that opening 22 and conduit 11 are eliminated in this embodiment.

Turning to FIG. 7, the further alternative embodiment shown therein has a balloon 24 at the distal end of catheter 10. Balloon 24 anchors the catheter by pressing against outer bladder wall 55 when inflated by fluid through opening 22'. Also, when inflated, balloon 24 serves to prevent leakage of fluid from bladder 50 along the outside of catheter 10 and into urethral canal 33. Balloon 23 can be fabricated and used in a manner similar to that disclosed in U.S. Pat. No. 4,579,554. Such a balloon catheter embodiment can either have a third lumen for inflating the balloon, or just two lumina can be provided as shown in FIG. 6. In the case of two lumina as shown in FIG. 6, one lumen serves solely to inflate balloon 23, and the other lumen 20 is for administering medication and for drainage of the bladder after bursting diaphragm 14, if drainage is required. Generally, when treating cancer by administering BCG, no separate provision for drainage is required, as the patient simply urinates normally after the procedure is completed.

After administration of BCG, the catheter is withdrawn completely and, after about two hours, the patient is allowed to urinate normally. Two hours is normally sufficient for the administered BCG to have caused the inflammation response that results in the sloughing off or the destruction of the tumor.

It will be understood that the above description of the present invention is susceptible to various modifications, changes, and adaptations, and such are intended to be comprehended within the meaning and range of equivalents of the claims.

What is claimed is:

1. A device for delivering medication into a human body, comprising:
   a catheter having proximate and distal ends;

a lumen extending substantially the entire length of said catheter;

means defining an opening in said catheter near said distal end, said opening being fluidly connected to said lumen for administering fluid to a body when said catheter is inserted therein; and a diaphragm disposed in said opening for blocking off said opening from said lumen, and said diaphragm being burstable by a predetermined pressure for unblocking said lumen for fluidly connecting said opening with said lumen.

2. A device as defined in claim 1, wherein said diaphragm includes means for causing said diaphragm to distend before bursting by the predetermined pressure.

3. A device as defined in claim 1, wherein said diaphragm is disposed in said lumen and spaced from said opening.

4. A device as defined in claim 1, wherein groove means is disposed on said diaphragm for causing said diaphragm to burst in a controlled manner by the predetermined pressure.

5. A device as defined in claim 1, wherein said diaphragm is burstable by a pressure less than the pressure required for causing said diaphragm to distend within a human urethra.

6. A device as defined in claim 1, further comprising a balloon disposed at said distal end, and means for inflating said balloon for anchoring said catheter in a human bladder.

7. A device for delivering medication into a human body, comprising:

a catheter having proximate and distal ends;

first and second lumina extending substantially the entire length of said catheter;

means defining a first opening in said catheter near said distal end, said first opening being fluidly connected to said first lumen for draining fluid from a body when said catheter is inserted therein;

means defining a second opening in said catheter between said first opening and said distal end of said catheter, and said second opening being fluidly connected with said second lumen; and a diaphragm disposed in said second opening for blocking off said second opening from said second lumen, and said diaphragm being burstable by a predetermined pressure for unblocking said second lumen for fluidly connecting said second opening with said second lumen.

8. A device as defined in claim 7, wherein said diaphragm includes means for causing said diaphragm to distend before bursting by the predetermined pressure.

9. A device as defined in claim 7, wherein said diaphragm is disposed in said second lumen and spaced from said second opening.

10. A device as defined in claim 7, wherein groove means is disposed on said diaphragm for causing said diaphragm to burst in a controlled manner by the predetermined pressure.

11. A device as defined in claim 7, wherein said diaphragm is burstable by a pressure less than the pressure required for causing said diaphragm to distend within a human urethra.

12. A device as defined in claim 7, further comprising a balloon disposed at said distal end, and means for inflating said balloon for anchoring said catheter in a human bladder.

13. A method of delivering concentrated bacillus Calmette-Guerin (BCG) vaccine into the bladder of bladder cancer patients for treating bladder cancer, said method comprising:

inserting a urethral catheter having a lumen extending substantially the entire length thereof through the urethra into the bladder; and applying a pressure for bursting a diaphragm disposed in and blocking the lumen for causing BCG to be administered into the bladder only after the diaphragm has been ruptured.

14. A method as defined in claim 13, wherein said pressure applying step comprises applying the pressure at a level that prevents distension and rupturing of the diaphragm when the diaphragm is in the urethra.

15. A method of delivering concentrated bacillus Calmette-Guerin (BCG) vaccine into the bladder of bladder cancer patients for treating bladder cancer, said method comprising:

inserting a urethral catheter having proximate and distal ends, said urethral catheter including:

first and second lumina extending substantially the entire length of said catheter;

means defining a first opening in said catheter near said distal end, said first opening being fluidly connected to said first lumen for draining fluid from a body when said catheter is inserted therein;

means defining a second opening in said catheter between said first opening and said distal end of said catheter, and said second opening being fluidly connected with said second lumen; and a diaphragm disposed adjacent to said second opening for blocking off said second opening from said second lumen, and said diaphragm being burstable by a predetermined pressure for unblocking said second lumen for fluidly connecting said second opening with said second lumen through the urethra into the bladder;

applying a pressure sufficient to distend and burst the diaphragm;

closing the first lumen; and introducing BCG vaccine through the second lumen, wherein the first lumen is closed before introducing BCG vaccine in order to prevent premature leakage of BCG vaccine.

16. A method as defined in claim 15, wherein said pressure applying step comprises applying the pressure at a level that prevents distension and rupturing of the diaphragm when the diaphragm is in the urethra.

* * * * *